United States Patent
Wang et al.

(10) Patent No.: US 11,666,210 B2
(45) Date of Patent: *Jun. 6, 2023

(54) SYSTEM FOR RECOGNIZING DIABETIC RETINOPATHY

(71) Applicants: SHENZHEN SIBIONICS TECHNOLOGY CO., LTD., Shenzhen (CN); SHENZHEN SIBRIGHT TECHNOLOGY CO., LTD., Shenzhen (CN)

(72) Inventors: Juan Wang, Shenzhen (CN); Bin Xia, Shenzhen (CN); Yujing Bai, Shenzhen (CN); Xiaoxin Li, Shenzhen (CN); Zhigang Hu, Shenzhen (CN); Yu Zhao, Shenzhen (CN)

(73) Assignees: SHENZHEN SIBIONICS TECHNOLOGY CO., LTD., Shenzhen (CN); SHENZHEN SIBRIGHT TECHNOLOGY CO., LTD., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/455,795

(22) Filed: Nov. 19, 2021

(65) Prior Publication Data

US 2022/0079430 A1 Mar. 17, 2022

Related U.S. Application Data

(63) Continuation of application No. 16/609,213, filed as application No. PCT/CN2017/095909 on Aug. 4, 2017, now Pat. No. 11,213,197.

(30) Foreign Application Priority Data

May 4, 2017 (CN) .......................... 201710306096.8

(51) Int. Cl.
*A61B 3/00* (2006.01)
*G06N 20/20* (2019.01)
(Continued)

(52) U.S. Cl.
CPC ............ *A61B 3/0025* (2013.01); *G06N 3/045* (2023.01); *G06N 3/08* (2013.01); *G06N 20/10* (2019.01);
(Continued)

(58) Field of Classification Search
CPC ...... A61B 3/0025; G06N 20/20; G06N 20/10; G06N 3/045; G06N 3/08; G06T 7/0012;
(Continued)

(56) References Cited

U.S. PATENT DOCUMENTS 10,610,098 B1 * 4/2020 Soliz .................... G06V 40/197
11,213,197 B2 * 1/2022 Wang ................... G06T 7/0014
(Continued)

FOREIGN PATENT DOCUMENTS

CN 105701468 A * 6/2016 ......... G06K 9/00228
CN 107358606 B 7/2018
(Continued)

*Primary Examiner* — Khai M Nguyen
(74) *Attorney, Agent, or Firm* — Avek IP, LLC

(57) ABSTRACT

Some embodiments of the disclosure provide an artificial neural network system for recognizing a lesion in a fundus image. The system includes a pre-processing module configured to pre-process a target fundus image and a reference fundus image taken from one person separately, a first neural network (12) configured to generate a first advanced feature set from the target fundus image, a second neural network (22) configured to generate a second advanced feature set from the reference fundus image, a feature combination module (13) configured to combine the first advanced feature set and the second advanced feature set to form a feature combination set, and a third neural network (14) configured (Continued)

to generate, according to the feature combination set, a judgmental result of lesions.

20 Claims, 8 Drawing Sheets

(51) Int. Cl.
*G06N 20/10* (2019.01)
*G06N 3/08* (2023.01)
*G06T 7/00* (2017.01)
*G06N 3/045* (2023.01)

(52) U.S. Cl.
CPC ........... *G06N 20/20* (2019.01); *G06T 7/0012* (2013.01); *G06T 2207/20081* (2013.01); *G06T 2207/20084* (2013.01); *G06T 2207/30041* (2013.01); *G06T 2207/30096* (2013.01)

(58) Field of Classification Search
CPC . G06T 2207/20081; G06T 2207/20084; G06T 2207/30041; G06T 2207/30096
See application file for complete search history.

(56) References Cited

U.S. PATENT DOCUMENTS

| | | | |
|---|---|---|---|
| 2015/0125052 A1* | 5/2015 | Wong | G06V 10/763 |
| | | | 382/128 |
| 2017/0112372 A1* | 4/2017 | Chakravorty | A61B 3/1241 |
| 2018/0293737 A1* | 10/2018 | Sun | G06N 3/08 |
| 2020/0349710 A1* | 11/2020 | Paschalakis | G06F 18/2411 |

FOREIGN PATENT DOCUMENTS

| | | |
|---|---|---|
| CN | 107423571 B | 7/2018 |
| CN | 108172291 B | 1/2020 |
| CN | 108553079 B | 6/2020 |
| JP | 6745496 B2 * | 8/2020 |

* cited by examiner

SYSTEM FOR RECOGNIZING DIABETIC RETINOPATHY

CROSS REFERENCE TO RELATED APPLICATIONS

This application is a continuation of U.S. application Ser. No. 16/609,213, filed on Oct. 29, 2019, which is the United States national stage entry under 35 U.S.C. 371 of PCT/CN2017/095909 filed on Aug. 4, 2017, and further claims the Chinese priority number 201710306096.8 filed on May 4, 2017, the disclosure of which are incorporated by references herein in their entireties.

FIELD OF THE DISCLOSURE

The present invention relates to the field of artificial neural networks, and more particularly to an artificial neural network and system for recognizing a lesion in a fundus image.

BACKGROUND

An artificial neural network is a machine learning model that simulates the human brain structure. With the development of artificial neural networks, especially artificial intelligence technology such as deep learning, the application of artificial neural networks in the field of medical image diagnosis is drawing more and more attention. By using such an artificial neural network, possible lesions can be automatically determined according to medical images, and automatic screening of the medical images can be completed. For example, extensive researches of artificial neural networks such as deep learning have been conducted in various fields, such as pathological examination of breast cancer, lung cancer detection, cardiovascular imaging and the like.

Medical images, which are usually obtained by means of a camera, an x-ray transmission machine, CT, OCT, MM, and the like, may contain numerous details of body structures or tissues, and by identifying such details in a medical image, it can help a doctor with relevant diagnosis. Taking fundus images among medical images for example, a fundus image contains abundant details of vitreous body, retinal, choroid and the like, and if there are related lesions, changes such as microangioma, bleeding, hard exudates and the like can be presented in the fundus image. Among those lesions, diabetic retinopathy, for example, as a common fundus lesion, is one of the diabetic complications, and has become one of the main causes of blindness of the working-age adults. It is estimated that in China, the existing diabetic patients are 92.4 million with a five-year incidence of 43% and the rate of blindness of 10%. Various researches indicate that early diagnosis and treatment of the diabetic retinopathy can effectively relieve or even improve the visual impairment of a patient. Therefore, regular fundus disease screening of diabetic patients is of great social significance. However, conventional diabetic retinopathy screening requires specialized ophthalmologists to identify fundus images by eyes to make a diagnosis and is not conductive to large-scale promotion for its large amount of work and high labor cost. Meanwhile, fundus screening requires a doctor to read a large number of fundus images in a short time, which may result in a reduction in diagnosis accuracy due to fatigue. Therefore, there is an urgent need for automatic screening (automatic image reading) by a computer through an artificial intelligence algorithm.

At present, scientific research teams have carried out similar researches. For example, non-patent document 1 discloses a method for diagnosing diabetic retinopathy by artificial intelligence, where related researches were carried out by utilizing the well-known deep learning network structure Inception-v3, and a high accuracy is achieved. It achieves at least the effect of replacing part of work of a professional ophthalmologist.

In addition, patent document 2 discloses a method, device and system for processing a fundus image based on deep learning. In the patent document 2, a conventional convolutional neural network is employed to identify and analyze an image. In particular, a resampled fundus image is used as an input, and a seven-layer convolutional neural network including five convolution layers and two fully connected layers is employed for identification.

REFERENCE DOCUMENTS

Non-patent document 1: Development And Validation Of A Deep Learning Algorithm For Detection Of Diabetic Retinopathy In Retinal Fundus Photographs, JAMA Nov. 29, 2016.
Patent document 2: Chinese patent application CN106408564A.

SUMMARY

However, in the prior art as described above, although deep learning methods have been employed to automatically identify fundus images for various diabetic retinopathy, such methods are still far from clinical application. For example, the Inception-v3 deep learning network structure employed in the method described in the non-patent document 1 is a network structure directed against natural image classification and target detection that requires the size of an input image to be 299×299 pixels, rather than particular medical images.

In addition, although the patent document 2 also relates to the processing of a fundus image, the purpose thereof is merely recognizing area image features rather than making a diagnosis on a fundus disease. Therefore, the fundus image processing method employed in the patent document 2 is quite far from the clinical level.

In view of the defects of the above prior art, the present invention aims at providing an artificial neural network and system for recognizing a lesion in a fundus image that can improve the accuracy of diagnosis of lesions in fundus images.

To this end, an aspect of the present invention provides an artificial neural network for recognizing a lesion in a fundus image which compromises a pre-processing module configured to separately pre-process a target fundus image and a reference fundus image taken from one person; a first neural network configured to generate a first advanced feature set from the target fundus image; a second neural network configured to generate a second advanced feature set from the reference fundus image; a feature combination module configured to combine the first advanced feature set and the second advanced feature set to form a feature combination set; and a third neural network configured to generate, according to the feature combination set, a diagnosis result of lesions.

In one aspect of the present invention, by using a target fundus image and a reference fundus image as independent input information separately, a diagnostic process of a doctor to make a diagnosis on the target fundus image with reference to the other fundus image of the same person can thus be simulated, thereby facilitating to improve the diagnosis accuracy of lesions in the fundus image.

Moreover, in the artificial neural network according to one aspect of the present invention, the target fundus image and the reference fundus image may be the same. In this case, even though one fundus image is used, a valid lesion diagnosis result can also be obtained.

Moreover, in the artificial neural network according to one aspect of the present invention, the first neural network and the second neural network may be the same. In this case, the number of parameters of the neural network can be controlled, thereby improving the training efficiency of the neural network and facilitating to inhibit over-fitting.

Moreover, in the artificial neural network according to one aspect of the present invention, optionally, the pre-processing module includes an area detection unit configured to detect designated fundus areas in the target fundus image and the reference fundus image; an adjustment unit configured to clip and resize the target fundus image and the reference fundus image; and a normalization unit configured to normalize the target fundus image and the reference fundus image. Thus, the target fundus image and the reference fundus image can be effectively pre-processed and the accuracy of subsequent extraction of image features by each neural network can be improved, thus improving the diagnosis result of lesions in the fundus image.

Moreover, in the artificial neural network according to one aspect of the present invention, optionally, the third neural network generates diagnosis results of lesions based on the feature combination set and patient information. Thus, it can be closer to an actual diagnostic process of a doctor so that the accuracy of diagnosis can be improved. Further, the third neural network may include a fully connected layer, and the patient information may be used as an input to the fully connected layer.

Moreover, in the artificial neural network according to one aspect of the present invention, optionally, the patient information includes at least one of age, gender, vision, and past medical history. In addition, the patient information may also include body weight. In this case, a diagnostic process of a doctor can be further simulated, and the accuracy of lesion diagnosis can be improved.

Moreover, in the artificial neural network according to one aspect of the present invention, optionally, the first neural network and the second neural network are convolutional neural networks. In this case, due to the advantages of both weight-sharing and local receptive view of the convolutional neural network, training of parameters can be greatly reduced, thereby increasing processing speed and saving hardware overhead.

In addition, another aspect of the present invention provides an artificial neural network for recognizing a lesion in a medical image which compromises a pre-processing module configured to separately pre-process a target medical image and a reference medical image taken from one person; a first neural network configured to generate a first advanced feature set from the target medical image; a second neural network configured to generate a second advanced feature set from the reference medical image; a feature combination module configured to combine the first advanced feature set and the second advanced feature set to form a feature combination set; and a third neural network configured to generate a diagnosis result of lesions from feature combination set.

In another aspect of the present invention, by using a target medical image and a reference medical image as independent input information respectively, a diagnostic process of a doctor to make a diagnosis on the target medical image with reference to the other medical image of the same person can thus be simulated, thereby facilitating to improve the judgment accuracy of lesions in the medical image.

In the artificial neural network according to another aspect of the present invention, optionally, the target medical image and the reference medical image are the same. In this case, even though only one fundus image of one person is obtained, the neural network can be trained effectively, and lesion diagnosis effect can be improved.

In addition, a further another aspect of the present invention provides an artificial neural network system including a plurality of artificial neural networks as described above; and a diagnostic device configured to synthesize results that are output from the plurality of artificial neural networks, respectively, and output a final diagnosis result.

Still further, other aspect of the present invention further provides a method for recognizing a lesion in a fundus image which compromises separately pre-processing a fundus image pair including a target fundus image and a reference fundus image; recognizing the target fundus image and the reference fundus image by deep learning to obtain features of the target fundus image and features of the reference fundus image; combining the features of the target fundus image with the features of the reference fundus image to form a feature sequence; recognizing the feature sequence by deep learning to obtain a diagnosis result of lesions in the fundus image. Therefore, a diagnostic process of a doctor to make a diagnosis on the target fundus image with reference to the other fundus image of the same person can be simulated, thereby facilitating to improve the diagnosis accuracy of lesions in the fundus image.

Moreover, in the method for recognizing a lesion in a fundus image according to other aspect of the present invention, optionally, the pre-processing includes area identification, image clipping, resizing and normalization.

Moreover, in the method for recognizing a lesion in a fundus image according to other aspect of the present invention, optionally, the pre-processing also includes data expansion for the fundus image pair during training.

According to the present invention, an artificial neural network and system for recognizing a lesion in a fundus image that can improve the screening accuracy of fundus lesions, and a method for recognizing a lesion in a fundus image can be provided.

BRIEF DESCRIPTION OF THE DRAWINGS

Illustrative embodiments of the disclosure are described in detail below with reference to the attached drawing figures.

DETAILED DESCRIPTION

Figure 1A:
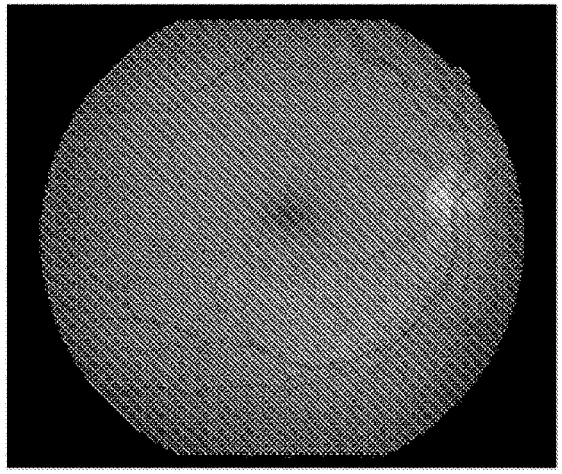
FIG. 1 is a schematic diagram illustrating lesion states in fundus images according to a first embodiment of the present invention, wherein FIG. 1 (a) shows an example of a normal-state fundus image, and FIG. 1 (b) shows an example of an abnormal fundus image.

Hereinafter, preferred embodiments of the present invention will be described in detail with reference to the accompanying drawings. In the following description, the same components are denoted by the same reference numerals, and the description thereof will not be repeated. In addition, the drawings are merely schematic views, and the ratio of the dimensions of the components to each other or the shape of the components may be different from the actual ones.

It should be noted that the terms "comprising" and "having", and any variants thereof, such as a process, method, system, product, or device, which are included or have a series of steps or units, are not necessarily limited to those steps or units are provided but may include or have other steps or units not explicitly listed or inherent to such processes, methods, products or devices.

In addition, the subtitles and the like referred to in the following description of the present invention are not intended to limit the content or scope of the present invention, but merely serve as a hint for reading. Such a subtitle cannot be understood as content for segmenting an article, nor should the content under the subtitle be limited to the scope of the subtitle.

The present invention relates to an artificial neural network and system for recognizing a lesion in a fundus image that can improve the screening accuracy of fundus lesions. Examples of processing fundus images by using deep neutral networks, such as a convolutional neural network, have been found in the prior art (see the above non-patent document 1 and patent document 2), however, as mentioned above, Inception-v3 is a network structure directed against natural image classification and target detection rather than particular medical images, thus there is still great room for improvement in accuracy on clinical screening of fundus images, such as diabetic retinopathy screening and the like. In addition, the fundus image processing method employed in the above patent document 2 is quite far from the clinical level.

Relatively, in the present invention, a target fundus image and a reference fundus image (which are hereinafter sometimes referred to as a "fundus image pair") are respectively used as independent input information. That is, with a reference to a "reference fundus image" of the same person for the recognition of fundus lesions in a "target fundus image", a condition of fundus lesions can be evaluated accurately and comprehensively. Here, the "target fundus image" refers to a fundus image in need of diagnosis for whether a lesion is present or what lesion is present, while the "reference fundus image" refers to a fundus image that, together with the "target fundus image", is taken from one and the same person. In the present invention, by using a target fundus image and a reference fundus image simultaneously, an actual diagnostic process of a doctor can be simulated, thereby improving the accuracy of fundus lesion diagnosis.

First Embodiment

Figure 1B:
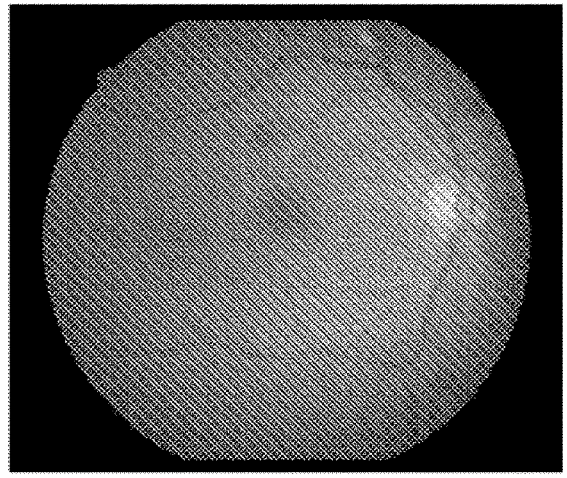
Figure 2A:
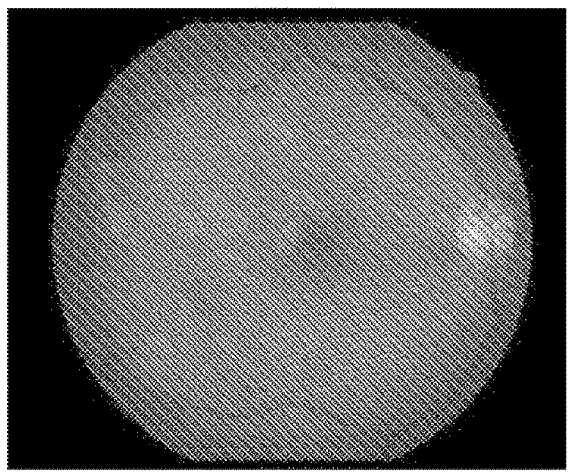
FIG. 2 is a schematic diagram illustrating examples of fundus images with fundus lesions according to the first embodiment of the present invention, wherein FIG. 2 (a) shows an example of a fundus image of diabetic retinopathy, and FIG. 2 (b) shows an example of a fundus image of hypertensive fundus lesions.
Figure 2B:
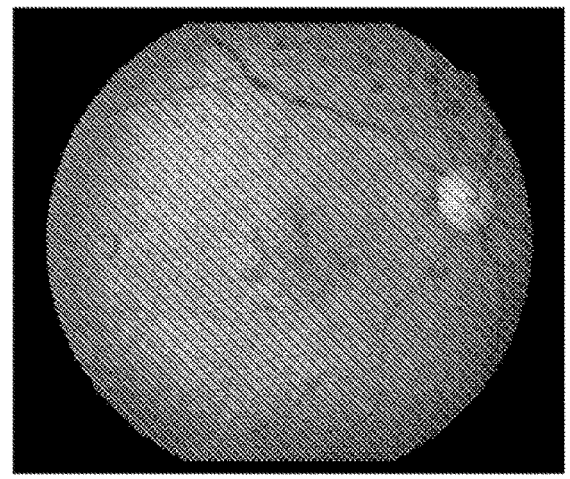

FIG. 1 is a schematic diagram illustrating lesion states in fundus images according to a first embodiment of the present invention, wherein FIG. 1 (*a*) shows an example of a normal-state fundus image, and FIG. 1 (*b*) shows an example of an abnormal fundus image. FIG. 2 is a diagram illustrating examples of fundus images with fundus lesions according to the first embodiment of the present invention, wherein FIG. 2 (*a*) shows an example of a fundus image of diabetic retinopathy, and FIG. 2 (*b*) shows an example of a fundus image of hypertensive fundus lesions.

In this embodiment, an artificial neural network and system according to this embodiment is enabled to learn a lesion-free fundus image (see FIG. 1 (*a*)) and a fundus image with lesions (see FIG. 1 (*b*)), and thus allowed to have the capability of determining whether a lesion is present in a fundus image. In addition, in this embodiment, the artificial neural network and system may also be enabled to further learn to determine a type of lesions and to grade lesions. Common fundus lesions include diabetic retinopathy (see FIG. 2 (*a*)), hypertensive and arteriosclerotic fundus lesions (see FIG. 2 (*b*)), age-related macular degeneration fundus lesions, retinal vein occlusion fundus lesions, retinal artery occlusion fundus lesions, high myopia fundus lesions, even cardiovascular diseases and other related fundus lesions and the like. The artificial neural network and system according to this embodiment can are especially suitable for the diabetic retinopathy of the fundus.

As mentioned above, the artificial neural network and system according to this embodiment can achieve unspecified categories of a disease-free diagnosis and a diagnosis of a disease existing and can also achieve categories to be classified of no disease and a specific disease type. In addition, the categories to be classified of the artificial neural network and network according to this embodiment may also be adjusted according to specific situations.

In some examples, when such an artificial neural network or system reaches the same judgmental level of a fundus doctor or the accuracy thereof (including sensitivity and specificity) meets a related diagnostic criteria, the artificial neural network or system can be used for assisting or replacing part of a doctor's work. The artificial neural network and system according to this embodiment can save a lot of time of a doctor on fundus screening (film reading time) and facilitate promotion and application of fundus screening, thereby promoting the development of health care, especially the primary health care.

Furthermore, the artificial neural network and system according to the present invention may also be easily promoted to recognize lesions in other medical images apart from lesions in fundus images, where the medical images may be, for example, X-ray photographs, ultrasound images, CT images, OCT images, MRI images, fluorescence angiogram images and the like that are taken from a human body or tissues.

Figure 3:
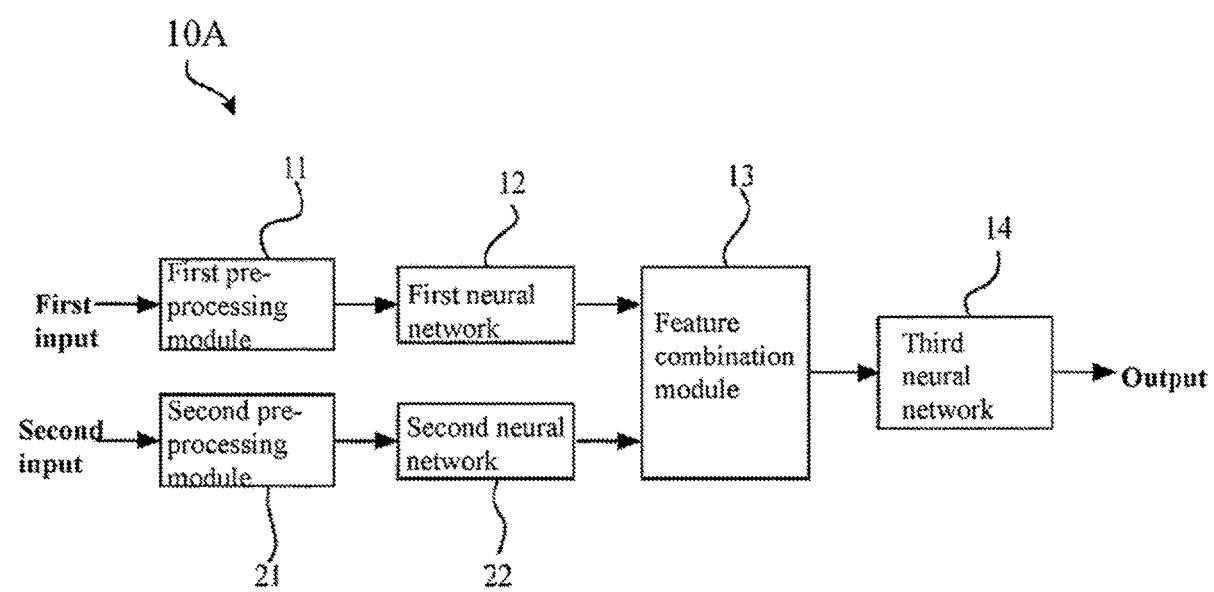
FIG. 3 is a schematic diagram showing an artificial neural network for recognizing a lesion in a fundus image according to the first embodiment of the present invention.

FIG. 3 is a schematic diagram showing an artificial neural network 10A for recognizing a lesion in a fundus image according to this embodiment. For example, as shown in FIG. 3, the artificial neural network 10A according to this embodiment may be used to recognize a lesion in a fundus image. In particular, the artificial neural network 10A may recognize a lesion in a fundus image by using a deep learning method.

It is well known that deep learning is one of machine learning methods, and the learning methods thereof is based on characterization of data. In deep learning, low-level features are combined to form a more abstract high-level representation attribute category or feature as to find the distributed feature representation of data. By means of the deep learning method, the accuracy of lesion recognition can be improved.

In this embodiment, the accuracy of lesion recognition can be reflected by sensitivity and specificity. Specifically, screening results may include true negative, true positive, false negative and false positive. True negative refers to that a fundus image shows normal, and a screening report also shows normal. True positive refers to that lesions are present in a fundus image and also shown in a screening report. False negative refers to that lesions are present in a fundus image, but a screening report shows normal. False positive refers to that a fundus image shows normal, but a screening report incorrectly displays a lesion. Thus, the sensitivity and the specificity are defined as follows, respectively:

$$\text{Sensitivity} = \frac{\text{True positives}}{\text{True positives} + \text{False negatives}} \times 100\%$$

$$\text{Specificity} = \frac{\text{True negatives}}{\text{True negatives} + \text{False positives}} \times 100\%$$

In general, the higher sensitivity and specificity are, the higher accuracy of lesion recognition will be. In some screening criteria, it may be already considered as a relatively reasonable screening mode when, for example, the sensitivity is over 80% and the specificity is 90%. In contrast, the artificial neural network and system according to this embodiment may have a sensitivity reaching 85% above and a specificity reaching 90% above.

In this embodiment, lesions in fundus images may include, but are not limited to, diabetic retinopathy, age-related macular degeneration fundus lesions, retinal vein occlusion fundus lesions and the like, and this embodiment may be especially well applied to the diabetic retinopathy.

Moreover, in this embodiment, the diagnosis of lesions in a fundus image may be achieved by rating. In some examples, primary rating and secondary rating may be employed. For example, a screening report provided by the artificial neural network 10A, and the system thereof may be taken as the primary rating, and then a doctor may make secondary rating based on the screening report. Therefore, a screening result of lesions can be obtained more accurately and reliably.

In this embodiment, a neural network structure employed in the artificial neural network 10A is not particularly limited. In some examples, the artificial neural network 10A according to this embodiment may be designed as a deep neural network. For example, the first neural network 12 and the second neural network 22 may adopt the structure of a deep neural network. In this case, abstract image features may be extracted from a particular medical image (such as a fundus image), thereby facilitating to diagnose lesions.

As shown in FIG. 3, the artificial neural network 10A according to this embodiment may include a pre-processing module, a first neural network 12, a second neural network 22, and a feature combination module 13, and a third neural network 14. Here, the pre-processing module may specifically include a first pre-processing module 11 and a second pre-processing module 21.

In this embodiment, the pre-processing module (the first pre-processing module 11 and the second pre-processing module 21) may be configured to separately pre-process a target fundus image and a reference fundus image (a fundus image pair) that are both taken from one person. That is, the first pre-processing module 11 may pre-process the target fundus image, while the second pre-processing module 21 may pre-process the reference fundus image. In addition, in this embodiment, the first pre-processing module 11 and the second pre-processing module 21 may be formed in one module and may also be formed as modules independently.

As mentioned above, in this embodiment, a target fundus image and a reference fundus image taken from the same person are used as inputs of diagnosis, that is, the target fundus image as a first input and the reference fundus image as a second input (see FIG. 3). As mentioned above, in this embodiment, for the diagnosis of fundus lesions in a target image, besides the target fundus image itself, a reference fundus image is used as a diagnostic reference. This process stimulates an actual situation where a doctor will make a comparison with and a reference to a plurality of fundus images at the same time in an actual diagnosis, and therefore, the diagnosis accuracy of lesions in a fundus image can be improved.

In addition, in the artificial neural network 10A according to this embodiment, the inventors of the present invention also take the following facts into account: 1) the same diagnosis result required be obtained for different images (including a target fundus image and a reference fundus image) taken from the same eye; 2) statistically, fundus lesions of the left and the right eye of one person (patient) are similar. Therefore, when making a diagnosis on a target fundus image, the diagnosis accuracy can be improved by using other fundus image from the same patient as assist.

Moreover, during the training or testing process of the artificial neural network 10A, two fundus images taken from a single eye (the left or right eye) of one person may be used in some examples. In this case, any one of the two fundus images may be used as the target fundus image and the other as the reference fundus image. In other examples, two fundus images respectively belongs to two eyes of one person may also be used. Similarly, in this case, any one of the two fundus images may be used as the target fundus image and the other as the reference fundus image.

Moreover, in the artificial neural network 10A according to this embodiment, in some examples, a target fundus image and a reference fundus image may be the same (that is, a first input and a second input may be the same). In this case, even though only one fundus image taken from a patient is used by the artificial neural network 10A according to this embodiment during the training or testing process, this fundus image may be used as the target fundus image and the reference target fundus separately. Thus, a valid lesion diagnosis result can also be obtained.

Moreover, four fundus images, including two fundus images taken from a left eye and two fundus images taken from a right eye, may also be used in this embodiment. In this case, any one of the four fundus images may be used as the target fundus images and the others as the reference fundus images.

In addition, in some examples, a plurality of fundus images may be obtained during the fundus image capture process. In this case, any one of the plurality of fundus images may be used as the target fundus images and the others as the reference fundus images. In other examples, numerically equal fundus images taken from left and right eyes may further be used.

Moreover, fundus images (including target fundus images or reference fundus images) used in this embodiment are not particularly limited and the fundus images can be color images (such as RGB images) and may also be gray images.

In this embodiment, a fundus image pair consisting of a target fundus image and a reference fundus image is used as inputs (including a first input and a second input). In this case, since the target fundus image and the reference fundus image (the fundus image pair) are similar or are same images, therefore, the subsequent screening capability of the artificial neural network can be improved by putting the target fundus image and the reference fundus image separately in a first neural network and a second neural network (that is, the target fundus image is used as the first input in the first neural network, and the reference fundus image as the second input in the second neural network, as shown in FIG. 3) to extract features of the fundus images.

Moreover, in the artificial neural network 10A according to this embodiment, a target fundus image and a reference fundus image may be fundus images of different eyes respectively. In this case, it may be conductive to improve the trained artificial neural network 10A so that the trained artificial neural network 10A can be closer to true diagnosis situations.

(Pre-Processing Module)

Figure 4:
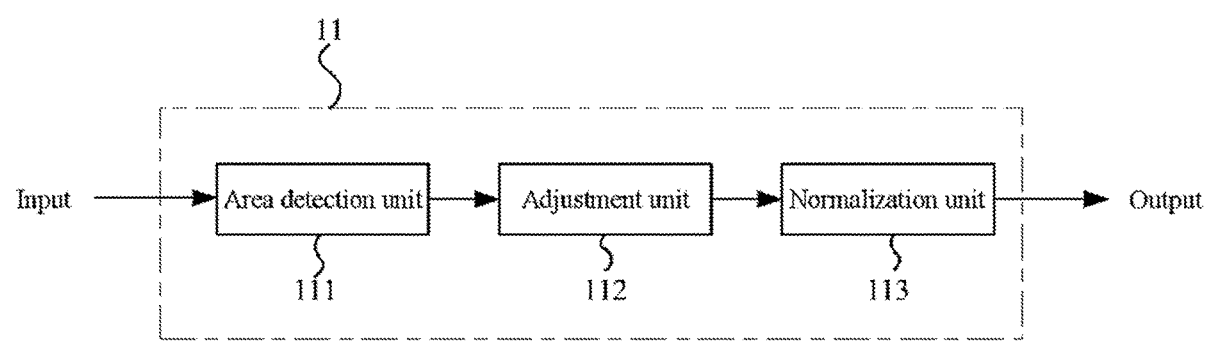
FIG. 4 is a block diagram showing the pre-processing module of the artificial neural network according to the first embodiment of the present invention.

FIG. 4 is a block diagram of a pre-processing module of the artificial neural network 10A according to this embodiment.

As mentioned above, the pre-processing module (including a first pre-processing module 11 and a second pre-processing module 21) may be configured to separately pre-process a target fundus image and a reference fundus image (a fundus image pair) that are both taken from one person. In particular, the first pre-processing module 11 and the second pre-processing module 21 may perform pre-processing such as fundus area detection, image clipping, resizing, normalizing and the like, for fundus images. That is, the first pre-processing module 11 may perform fundus area detection, image clipping, resizing, normalizing, and the like for the target fundus image, and the second pre-processing module 21 may perform fundus area detection, image clipping, resizing, normalizing, and the like for the reference fundus image.

In this embodiment, since the first pre-processing module 11 and the second pre-processing module 21 may be set as the same module, therefore, the first pre-processing module 11 will be described below in detail, and the second pre-processing module 21 may be completely the same in structure with the first pre-processing module 11.

As shown in FIG. 4, the first pre-processing module 11 of the artificial neural network 10A mainly includes an area detection unit 111, an adjustment unit 112 and a normalization unit 113.

In the first pre-processing module 11, the area detection unit 111 can detect fundus areas from various fundus images. In this embodiment, a fundus area to be detected may be, for example, a fundus area centered on an optic disk, or a fundus area including an optic disk and centered on a macula, or the like. In this embodiment, any area, whether centered on an optic disk or including the optic disk and centered on a macula, can show fundus lesions effectively. In some examples, the area detection unit 111 can detect a specific area in a fundus image by, for example, a sampling threshold method or Hough transform for later use by the artificial neural network. For example, referring to the fundus images shown in FIG. 1 (a) and FIG. 1 (b) and the like, the brightest circle in any fundus image is the optic disk, and the darkest area is the macula or retina fovea, together with blood vessels leading out from the optic disk.

In addition, as shown in FIG. 4, the adjustment unit 112 may be configured to clip and resize a fundus image (a target fundus image). Due to different sizes of the human eyes and different fundus camera devices used, the obtained fundus images may vary in resolution, fundus area size and the like. Therefore, it is necessary to resize such fundus images. For example, with the adjustment unit 112, a fundus image may be clipped according to a specific specification. In some examples, a square fundus image may be obtained by clipping. Moreover, a fundus image in this embodiment is not limited to square, and may also be, for example, rectangular, round, oval and the like. Further, the adjustment unit 112 can also perform other processing on a fundus image including, for example, distinguishing a fundus area from a patient information area in a fundus image (e.g., some fundus images may include names, medical insurance numbers and the like), and resizing fundus images processed by different fundus camera devices using different algorithms to solve problems such as uniformizing fundus background.

In addition, in some examples, the adjustment unit 112 can resize a fundus image to a specified size (e.g., pixel size), such as 256×256, 512×512, 1024×1024 pixels and the like. However, this embodiment is not limited thereto, and depending on particular requirements, the size of a fundus image can also be a size (pixel size) of any other specification, such as 128×128, 768×768, 2048×2048 pixels and the like.

Although there are no limitations to the size of a fundus image in this embodiment, considering more accurately recognizing more details of a fundus image, the size of a fundus image in this embodiment is preferably higher than or equal to 512×512 pixels. The deep learning framework Inception-v3 involved in the patent document 1 as mentioned above uses an image of only 299×299 pixels. However, since the feature of many fundus diseases (such as the features of early lesions of the diabetic retinopathy) may not obviously shown at such a pixel level, in this case, it may result in loss of important image detail information, for example, loss of low-grade fundus lesion (such as first-grade diabetic retinopathy) information during a subsequent down-sampling process (especially in large-scales down-sampling). Based on this, in the patent document 1, the first-grade diabetic retinopathy is treated as a healthy eye, which may thus lead to insufficient diagnosis of lesions in a fundus image and poor clinical effect. In contrast, in this embodiment, by limiting the size of a fundus image as described above, the loss of detail information of a fundus image can be effectively inhibited and thus improving diagnosis accuracy of fundus lesions.

In addition, in the first pre-processing module 11, the normalization unit 113 may be configured to normalize a fundus image (a target fundus image). Due to the difference in the fundus between different races and fundus imaging devices or conditions, fundus images may greatly vary, and therefore, it is necessary to perform normalization processing on the images.

In this embodiment, the normalization way of the normalization unit 113 is not particularly limited. For example, a zero mean, a unit standard deviation and the like may be adopted for normalization. In addition, in some examples, the normalization may be within of range of [0, 1]. By normalization, the difference of different fundus images can be overcome, and the performance of the artificial neural network can be improved.

Figure 5:
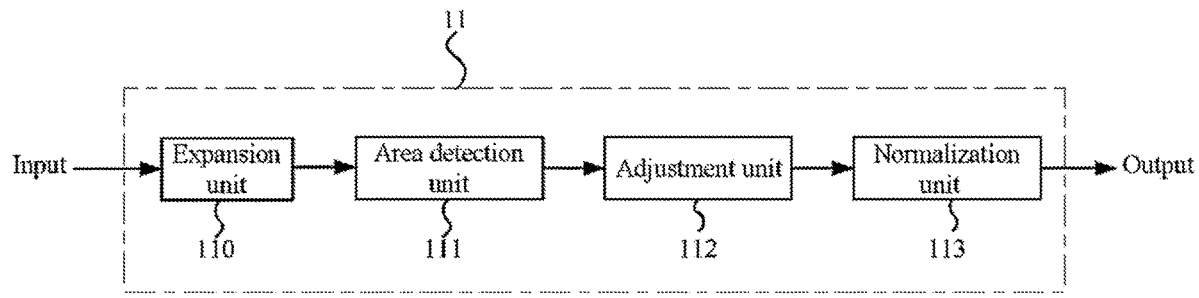
FIG. 5 is a schematic diagram showing a variation of the pre-processing module in FIG. 4.

FIG. 5 is a schematic diagram showing a variation of the pre-processing module 11 according to this embodiment. As shown in FIG. 5, the first pre-processing module 11 may also have an expansion unit 110. The expansion unit 110 may be disposed ahead of the area detection unit 111, which is not limited thereto in this embodiment.

In this embodiment, the expansion unit 110 may be configured for data expansion on a fundus image at the training phase of the neural network. With the expansion unit 110, data expansion may be performed on an obtained fundus image (a target fundus image) to increase a sample size of fundus images, thereby facilitating to overcome the over-fitting problem and improve the performance of the artificial neural network. In addition, what needs to be noted is that the expansion unit 110 is generally limited to expand data samples at the training phase of the neural network as described later and may not be used at the testing phase of the neural network.

In addition, there are no particular limitations to the expansion way taken by the expansion unit 110. For example, in some examples, sample expansion may be achieved through various image transformation of a fundus image. Such image transformation ways may include symmetric transformation, inverse transformation, rotation transformation, pixel translation and the like, and may also include adjustment of contrast, brightness, color, sharpness and the like of an image.

The configuration and functionality of the first pre-processing module 11 have been described above, and similarly, the second pre-processing module 21 may also have the same configuration and functionality with the first pre-processing module 11. In this case, a reference fundus image as a second input can be effectively pre-processed through the second pre-processing module 21, so that the artificial neural network (the second neural network and the third neural network) can process the reference fundus image subsequently.

As mentioned above, a target fundus image and a reference fundus image can be effectively pre-processed, respectively, by means of the first pre-processing module 11 and the second pre-processing module 21, thereby facilitating subsequent further processing (such as feature extraction and the like) on fundus images by each neural network.

(First/Second Neural Network)

In this embodiment, the first neural network 12 may be configured to generate a first advanced feature set from a pre-processed target fundus image. Similarly, the second neural network 22 may be configured to generate a second advanced feature set from a pre-processed reference fundus image. The first neural network and the second neural network may achieve abstract description of the target fundus image and the reference fundus by, for example, combining a plurality of layers of low-level features (pixel-level features). Here, the advanced features are merely relative to primary features (e.g., pixel-level features) of an original image after being processed by the artificial neural network, and not intended to precisely describe that such features are advanced. However, in general, after being processed by the neutral network, a tendency of being more high-level and abstract will be shown as the layer of the neutral network gets deeper. In addition, a feature set generally refers to including two or more than two features and may sometimes be referred to as a "feature matrix" in the present invention. Moreover, in some special cases, a feature set may also have only one feature, for example, an intermediate result, and then a "feature set" may refer in particular to a single "feature".

In addition, in this embodiment, the first neural network 12 and the second neural network 22 may both be designed as a convolutional neural network (CNN). Due to the advantages of weight-sharing, local receptive field and the like of the convolutional neural network, training of parameters can be greatly reduced, and may therefore increase processing speed and save hardware overhead. Additionally, the convolutional neural network can perform image recognition more effectively.

Figure 6:
FIG. 6 is a schematic diagram showing a network structure example of the artificial neural network according to the first embodiment of the present invention.
Figure 7:
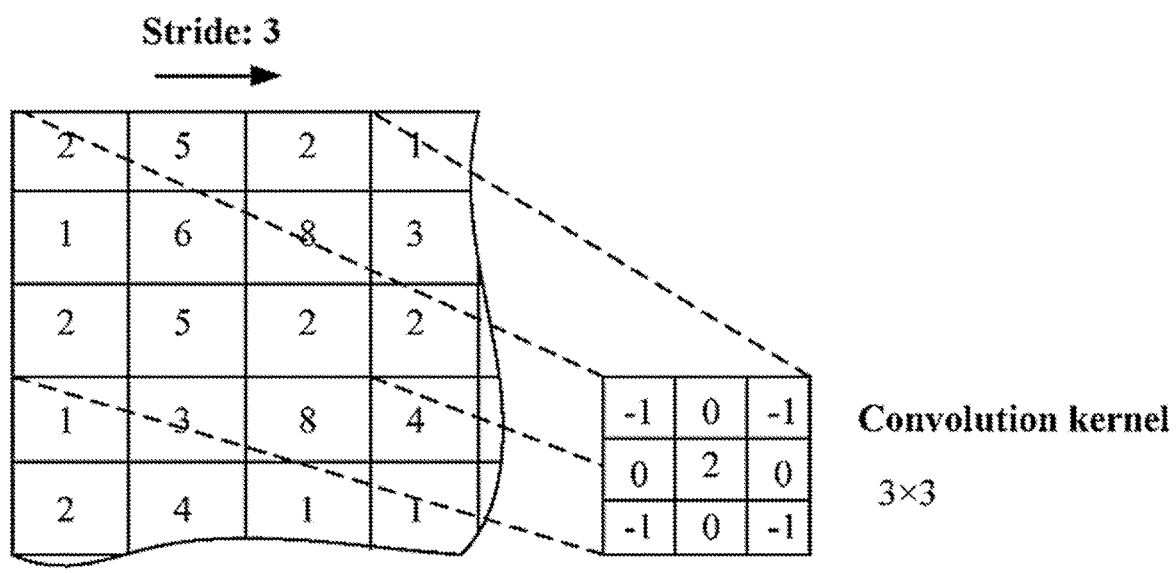
FIG. 7 is a schematic diagram showing an example of a convolution kernel employed in the artificial neural network in FIG. 6.

FIG. 6 is a schematic diagram showing a network structure example of the artificial neural network according to the first embodiment of the present invention. FIG. 7 is a schematic diagram showing an example of a convolution kernel employed in the artificial neural network in FIG. 6.

In some examples, convolutional neural networks may be used as the first the neural network 12 and the second neural network 22 respectively. For example, the network structures of the first neural network 12 and the second neural network 22 may be designed as neural network structures as shown in FIG. 6 and FIG. 7 (simplified representation):

-C1-S1-C2-S2-C3-S3-C4-

Here, C (including C1, C2, C3, and C4) represents a convolution layer, and S (including S1, S2, and S3) represents a pooling layer (sometimes referred to as a "down-sampling layer"). In some examples, except layer C1 that uses a 5×5 convolution kernel, each of the other convolution layers may use a 3×3 convolution kernel. In this case, for a medical image (a fundus image) of a specified size, such as 256×256 and 512×512 pixels, increase of training parameters can be greatly inhibited, and the training efficiency can be improved.

In addition, in the above convolutional neural network, the way of pooling may be max-pooling, mean-pooling, stochastic-pooling, and the like. With the pooling operation, on one hand, reduced dimensionality and improved operation efficiency can be achieved. Additionally, the neural network can be enabled to extract more abstract high-level features, thereby improving the diagnosis accuracy of fundus lesions.

In addition, in the above convolutional neural network, the number of convolution layers and the number of pooling layers may also be increased correspondingly according to the situation. In this case, the neural network can also be enabled to extract more abstract high-level features to further improve the diagnosis accuracy of fundus lesions.

In addition, in the artificial neural network 10A according to this embodiment, the first neural network 12 and the second neural network 22 may be completely the same. Specifically, the network structure of the first neural network 12 and the network structure of the second neural network 22 may be completely the same. In this case, the number of parameters of the artificial neural network can be reduced, thereby facilitating to inhibit over-fitting of the neural network.

In addition, the convolutional neural network structure used for the first neural network 12 and the second neural network 22 is not limited thereto, and other convolutional neural network structures can also be adopted as long as advanced features can be extracted from original fundus images (a target fundus image and a reference fundus image). Moreover, it is noted that the first neural network 12 and the second neural network 22 according to this embodiment are mainly intended for feature extraction and not for directly outputting a lesion diagnosis result.

(Feature Combination Module)

In this embodiment, as shown in FIG. 3, the feature combination module 13 may be configured to combine a first advanced feature set generated by the first neural network 12 and a second advanced feature set generated by the second neural network 22 to form a feature combination set. Here, the "feature set" in this embodiment may refer to a "feature sequence", a "feature vector", a "feature value set" and the like, and the meaning thereof should be understood in the broadest manner.

In some examples, the feature combination module 13 may combine a first advanced feature set and a second advanced feature set to form a one-dimensional feature vector (a feature combination set). In addition, in other examples, the feature combination module 13 may also calculate differences between a first advanced feature set and a second advanced feature set to obtain a feature combination set. Further, in other examples, the feature combination module 13 may also calculate mean values of a first advanced feature set and a second advanced feature set to obtain a feature combination set. Further, in other examples, the feature combination module 13 may perform linear or nonlinear transformation on a first advanced feature set and a second advanced feature set to obtain a feature combination set and the like.

In this embodiment, the features generated from the first neural network 12 and the features generated from the second neural network 22 can be combined by the feature combination module 13, thereby facilitating subsequent processing by the third neural network 14.

(Third Neural Network)

In this embodiment, the third neural network 14 may be configured to generate a diagnosis result of lesions according to the result of feature combination (a feature combination set). As shown in FIG. 3, the third neural network 14 may produce a diagnosis result on the input target fundus image based on a result obtained by the feature combination module 13. That is, the third neural network 14 generates a diagnosis result of lesions according to a feature combination set.

In this embodiment, the output dimensions of the third neural network 14 are consistent with categories to be classified (e.g., a lesion type). That is, for example, when the categories to be classified are a disease-free category and a disease existing category, the output dimensions of the third neural network 14 may be 2; and if the categories to be classified are a disease-free category and specific symptoms (e.g., 5 symptoms), the output dimensions of the third neural network 14 may be 6. In addition, the output dimensions of the third neural network 14 can be adjusted according to the actual situation.

In some examples, the outputs of the third neural network 14 may be values (percentages) between 0 and 1, and such values may each be interpreted as a probability that a target fundus image is classified into a particular category (lesion type). Then, the sum of the outputs of the third neural network 14 is 1 (probability sum).

In this embodiment, an output probability of the third neural network 14 is used for achieving final diagnoses. In some examples, when the probability of a particular category is the highest, it is determined that the fundus has lesions of the corresponding category. For example, if the probability of no lesion among all categories to be classified is the highest, the target fundus image is determined to be lesion-free. If the probability of diabetic retinopathy is the highest, the target fundus image is then determined to be diabetic retinopathy.

In addition, the network structure of the third neural network 14 is not particular limited. In some examples, the third neural network 14 may use a convolution layer, a fully connected layer and other auxiliary layers (such as a batch normalization layer, a pooling layer and the like). For example, in some cases, the output layers of the third neural network 14 may include a single convolution layer, two fully connected layers and an output layer (softmax layer). Moreover, in other cases, the output layers of the third neural network 14 may also adopt two convolution layers, two pooling layers, three fully connected layers, and an output layer (e.g., a softmax layer).

As mentioned above, in this embodiment, by using a target fundus image and a reference fundus image as independent input information respectively, extraction of advanced features from the target fundus image by the first neural network and extraction of advanced features from the reference fundus image by the second neural network can be facilitated. Furthermore, the advanced features that are obtained from the first neural network and the second neural network, respectively, are combined and then a diagnosis result of lesions is obtained by the third neural network. Thus, the diagnostic performance of lesions in a fundus image can be significantly improved.

(Training and Testing)

In this embodiment, the first neural network 12, the second neural network 22 and the third neural network 14 can be trained together to obtain an optimal neural network structure. For example, where convolutional neural networks are used as a first neural network 12 and a second neural network 22, when the above described neural networks are trained, the convolutional neural networks can be trained by using a fundus image pair (including a target fundus image and a reference fundus image) of the training set.

Moreover, as described, the first neural network 12, the second neural network 22 and the third neural network 14 according to this embodiment can be trained together, but the embodiment is not limited thereto. For example, the first neural network 12 and the second neural network 22 may be trained first by the way of training an auto-encoder network and then be trained together with the third neural network 14.

In addition, in this embodiment, for the fundus images, during the training or testing process of the artificial neural network 10A, two fundus images of a single eye from one person may be used, and two fundus images of two eyes from one person may also be used.

Furthermore, during the training or testing process of the artificial neural network 10A, four fundus images comprising two fundus images taken from the left eyes and two fundus images taken from the right eye may also be used. In this case, it may better match the actual situation of diagnosis of lesions in a fundus image. Incidentally, the international popular gold standard for diagnosis of lesions in fundus images at present is using seven fundus images of different fundus areas and having a visual angle of 30 degrees. However, the inventors of the present invention have found in long-term practice that an equivalent lesion diagnosis effect may also be achieved by using, for example, four fundus images from two eyes which have specified areas and a visual angle of 45 degrees.

Additionally, this embodiment is not limited thereto, and more fundus images taken from two eyes of one person may also be used. More preferably, numerically equal fundus images taken from left and right eyes are used.

During the training process of the artificial neural network 10A according to this embodiment, 50-200 thousand fundus images from a cooperative hospital and having patient information removed are selected as a training set, for example, 5000-20000 fundus images as a testing set. During the training or testing process, the fundus images are unified to RGB color fundus images in a size of, for example, 512×512 or 1024×1024 pixels.

During the training process, parameters are adjusted by using the stochastic gradient descent method, thereby obtaining a final training result. Then, the trained artificial neural network 10A is employed to recognize fundus images in the testing set, obtaining an average recognition accuracy of, for example, 90% and above. It thus can be seen that the artificial neural network 10A according to this embodiment can obtain an improved lesion diagnosis accuracy with consideration of the fundus clinical circumstance.

(Lesion Recognition Process)

Figure 8:
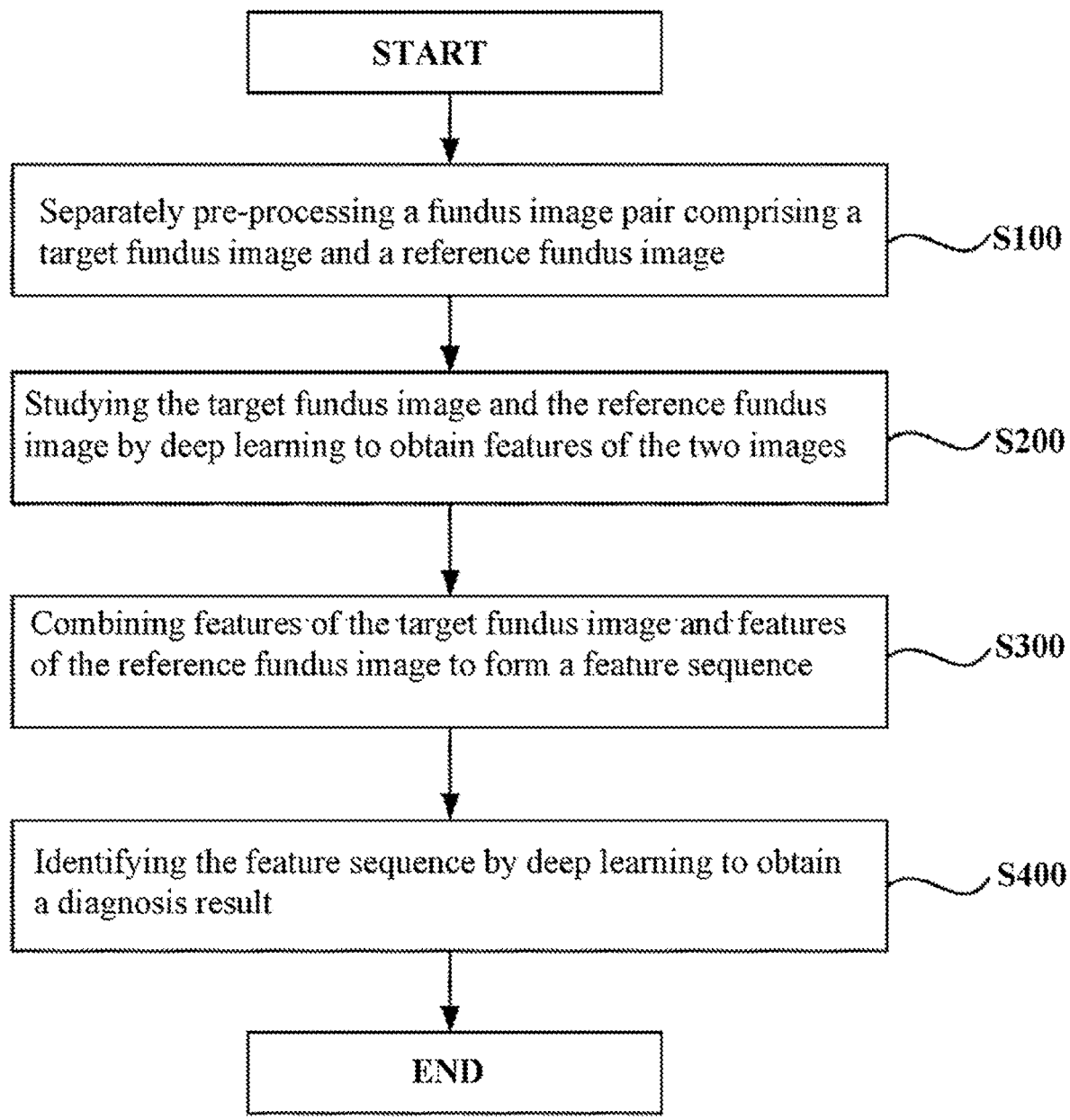
FIG. 8 is a block diagram of an artificial neural network system according to the first embodiment of the present invention.

FIG. 8 is a flowchart showing a method for recognizing a lesion in a fundus image using the artificial neural network 10A according to this embodiment. Hereinafter, with reference to FIG. 8, the method for recognizing a lesion in a fundus image using the artificial neural network 10A according to this embodiment will be described below in detail.

In the method for recognizing a lesion in a fundus image according to this embodiment, first, separately pre-processing is performed on a fundus image pair comprising a target fundus image and a reference fundus image (step S100) to obtain fundus images satisfying specified conditions.

In step S100, for example, area detection, image clipping, resizing, normalization and the like may be performed on the fundus image. In addition, in step S100, data expansion may also be performed on the fundus image pair (including the target fundus image and the reference fundus image) during neural network training to increase the size of data samples for training, thereby improving the accuracy of diagnosis of fundus lesions. In some examples, the target fundus image and the reference fundus image may be the same image.

Then, after the step S100, respective operations may be performed on the target fundus image and the reference fundus image by using the deep learning method so as to obtain the features of the target fundus image and the features of the reference fundus image (step S200). In step S200, advanced features of the target fundus image and advanced features of the reference fundus image may be obtained by means of, for example, convolutional neural network. Since the convolutional neural network has the advantages of local receptive field and weight-sharing and is conducive to extraction of advanced features of a fundus image, the operation efficiency can be improved, and the hardware overhead can be saved.

After step S200, the features of the target fundus image and the features of the reference fundus may be combined to form a feature combination set (step S300). As described above, forming a feature combination set is beneficial for the synthesis of the features of the target fundus image and the features of the reference fundus image, thereby facilitating subsequent classification and diagnosis.

Finally, the feature combination set may be recognized by using a deep learning method so as to obtain a diagnosis result of lesions in the fundus image (step S400). In step S400, the diagnosis result of fundus lesions may be obtained by using, for example, an average operator, a maximum operator, logistic regression, random forest, and a support vector machine (SVM) and the like.

(Artificial Neural Network System)

Figure 9:
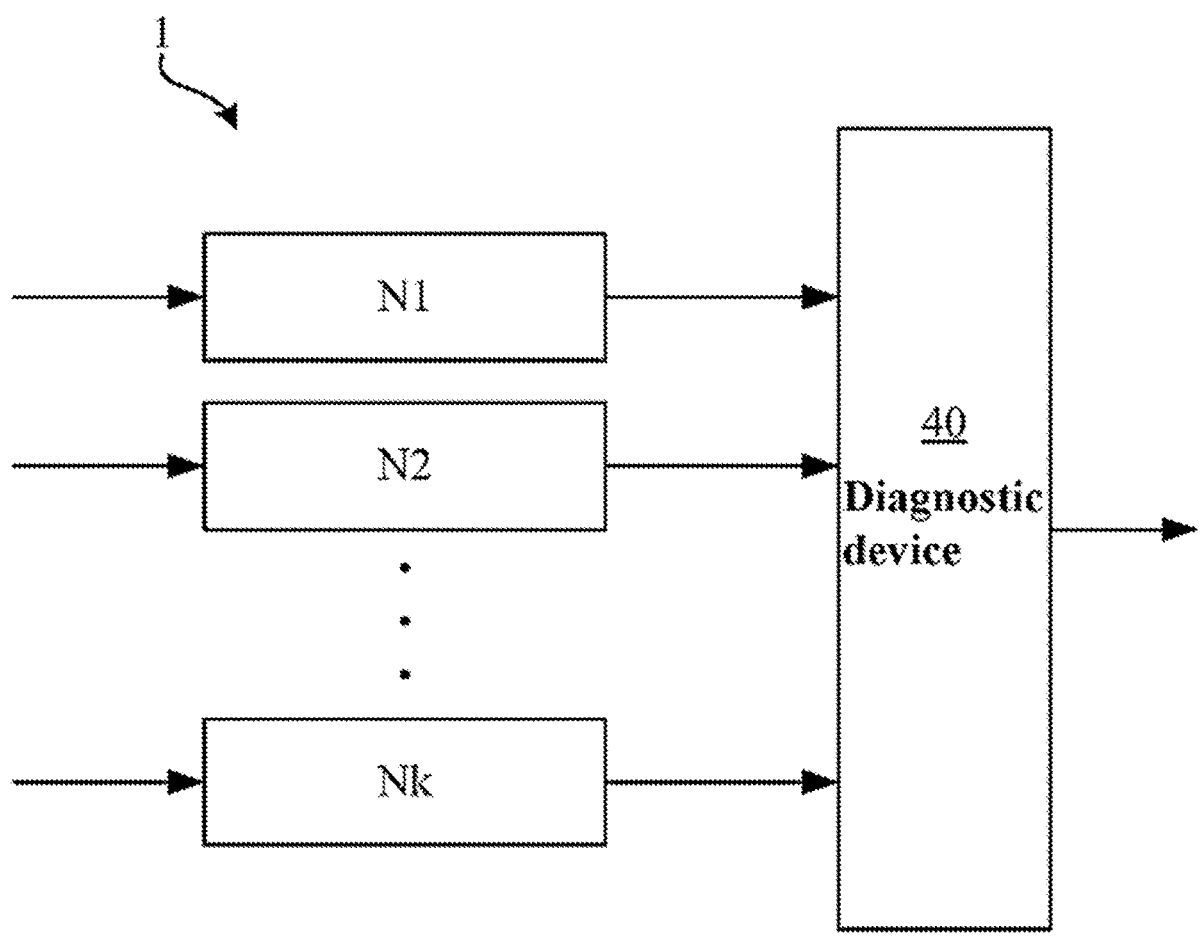
FIG. 9 is a flowchart showing a method for recognizing a lesion in a fundus image by the artificial neural network according to the first embodiment of the present invention.

FIG. 9 is a block diagram of an artificial neural network system 1 according to the first embodiment of the present invention.

In this embodiment, as shown in FIG. 8, a plurality of artificial neural networks Ni($1 \le i \le k$), such as artificial neural network N1, artificial neural network N2, artificial neural network N3, . . . , and artificial neural network Nk (k networks, $k \ge 2$), and a diagnostic device 40 may be combined to form an artificial neural network system 1. That is, the artificial neural network system 1 may include a plurality of artificial neural networks (the above artificial neural network N1, artificial neural network N2, artificial neural network N3, . . . , and artificial neural network Nk), and a diagnostic device 40. The above artificial neural network (artificial neural network N1, artificial neural network N2, artificial neural network N3, . . . , artificial neural network Nk) may be the artificial neural network 10A.

In this embodiment, inputs of the artificial neural network Ni ($1 \le i \le k$) may be different target fundus image and reference fundus image (a fundus image pair) corresponding to one eye of one person.

In addition, in some examples, each artificial neural network Ni ($1 \le i \le k$) may be the artificial neural network 10A. In particular, different artificial neural networks 10A that use the same fundus image pair may be used as the artificial neural networks Ni ($1 \le i \le k$).

In this embodiment, the diagnostic device 40 may synthesize the results output by the above plurality of artificial neural networks Ni ($1 \le i \le k$) and output a final diagnosis result. That is, the outputs of the above plurality of artificial neural networks (the above artificial neural network N1, artificial neural network N2, . . . , and artificial neural network Nk) are connected to the diagnostic device 40, and the diagnostic device 40 outputs the final diagnosis result by synthesizing the output results.

In some examples, the diagnostic device 40 may output a diagnosis result of whether there is a disease. In other examples, the diagnostic device 40 may output a diagnosis result of whether there is a disease and further, may output a diagnosis result of which type the fundus lesion belongs to if there is a disease.

In some examples, the diagnostic device 40 may determine a diagnosis result by outputting a probability. In addition, the method of the diagnostic device 40 may be various linear or nonlinear classifiers, such as Logistic Regression, Random Forest, Support Vector Machine (SVM), Adaboost and the like. In some examples, the diagnostic device 40 may also be some simple numerical operators, such as Average Operator, Maximum Operator, and the like.

Second Embodiment

Figure 10:
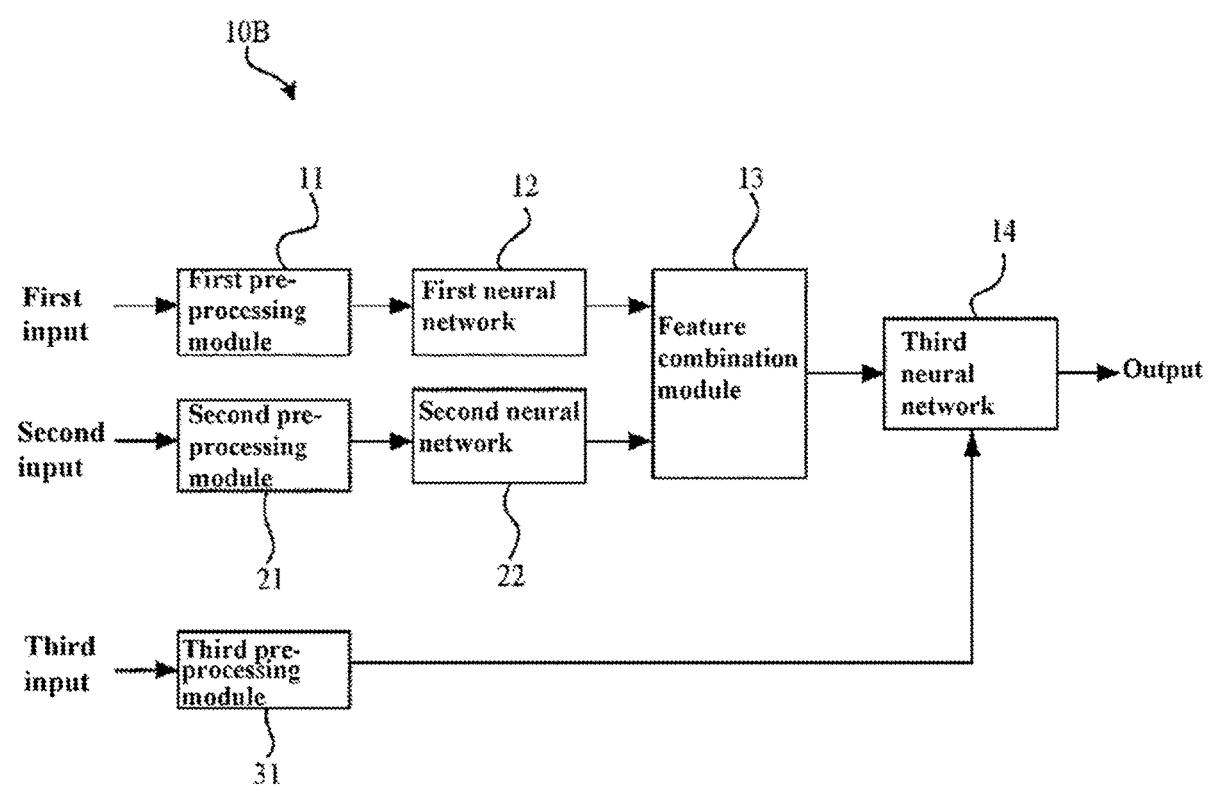
FIG. 10 is a block diagram showing an artificial neural network according to a second embodiment of the present invention.
Figure 11:
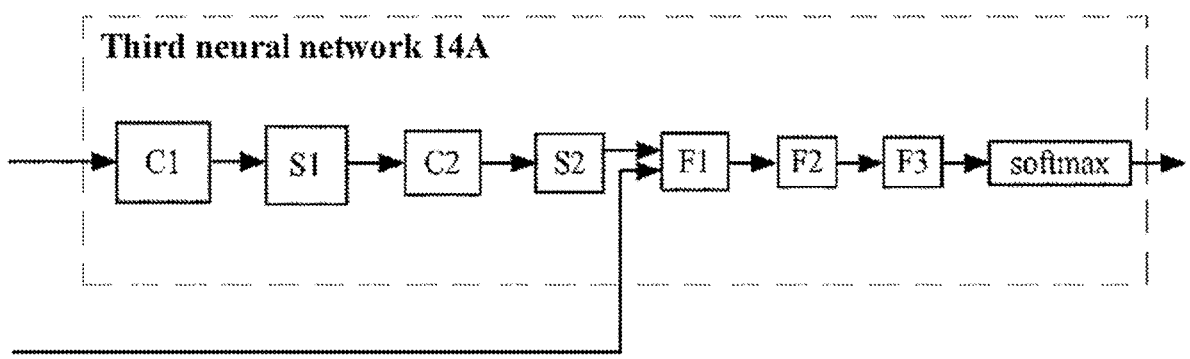
FIG. 11 is a schematic diagram illustrating an example of a third neural network according to the second embodiment of the present invention.
Figure 12:
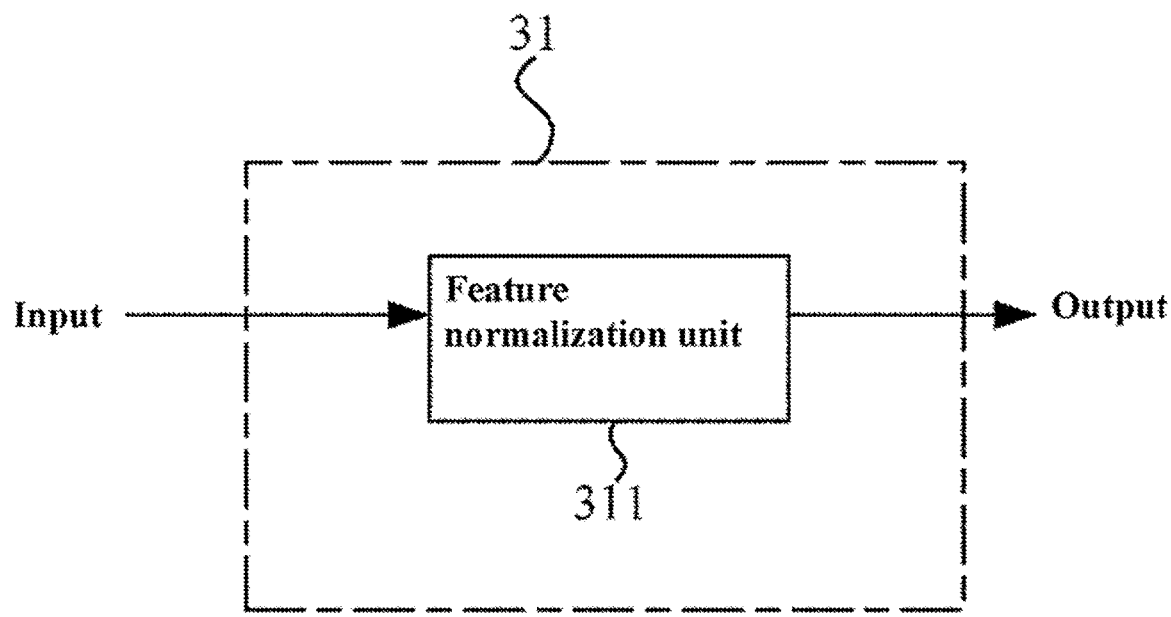
FIG. 12 is a block diagram showing a pre-processing module of the artificial neural network according to the second embodiment of the present invention.

FIG. 10 is a block diagram showing an artificial neural network 10B according to the second embodiment of the present invention. FIG. 11 is a diagram illustrating an example of a third neural network 14 according to the second embodiment of the present invention. FIG. 12 is a block diagram showing a pre-processing module 31 of the artificial neural network 10B according to the second embodiment of the present invention.

The difference between the artificial neural network 10B according to this embodiment and the artificial neural network 10A according to the first embodiment is that the artificial neural network 10B includes the pre-processing module 31, and the third neural network 14 may generate a diagnosis result of lesions according to the above feature combination set and patient information (see FIG. 10). The artificial neural network 10B according to this embodiment can also improve the accuracy (including sensitivity and specificity) of screening of fundus lesions.

The feature combination set has been described in detail in the first embodiment, and thus will not be redundantly described herein. In this embodiment, the feature combination set obtained by the feature combination module 13 is input into the third neural network 14. Further, the third neural network 14 generates a diagnosis result of lesions according to the feature combination set and patient information.

In this embodiment, the output dimensions of the third neural network 14 are consistent with categories to be classified (e.g., a lesion type). That is, for example, when the categories to be classified are a disease-free category and a disease existing category, the output dimensions of the third neural network 14 may be 2; and if the categories to be classified are disease-free and specific symptoms (e.g., 5 symptoms), the output dimensions of the third neural network 14 may be 6. In addition, the output dimensions of the third neural network 14 can be adjusted according to the actual situation.

In some examples, the outputs of the third neural network 14 may be values (percentages) between 0 and 1, and such values may each be interpreted as a probability that a target fundus image is classified into a particular category (lesion type). Then, the sum of the outputs of the third neural network 14 is 1 (probability sum).

In this embodiment, an output probability of the third neural network 14 is used for achieving final diagnoses. In some examples, when the probability of a particular category is the highest, it is determined that the fundus has lesions of the corresponding category. For example, if the probability of no lesion among all categories to be classified is the highest, the target fundus image is determined to be lesion-free. If the probability of diabetic retinopathy is the highest, the target fundus image is determined to be diabetic retinopathy.

In addition, in some examples, the patient information includes at least one of a patient's visual acuity, age, gender, and past medical history. Moreover, the patient information may also include body weight. According to the findings of the inventors of the present invention in years of ophthalmic practice, a patient's visual acuity, age, gender, past medical history, body weight and the like are all closely related to fundus lesions. That is, factors such as a patient's visual acuity, age, gender, past medical history and the like are also important reference factors for fundus lesion diagnosis.

Furthermore, the artificial neural network 10B may include a third pre-processing module 31 by which the patient information may be pre-processed. The third pre-processing module 31 may include a feature normalization unit 311 by which, for example, the values included in the patient information can be normalized to an interval of [0, 1], thereby avoiding possible adverse effects of the patient information on subsequent processing by the neural network.

In this embodiment, patient information is added to the artificial neural network 10B and provided as a third input to the third neural network 14A so as to improve the lesion recognition capability of the artificial neural network 10B. In the third neural network 14, apart from the features output by the feature combination module 13 used as inputs to the third neural network 14, patient information is output as features to the third neural network 14. Therefore, the third neural network 14 can generate a diagnosis result of lesions according to the feature combination set and the patient information.

In addition, the network structure of the third neural network 14 is not particularly limited. In some examples, the third neural network 14 may be implemented by using various combinations of a convolution layer, a fully connected layer and other auxiliary layers (such as a batch normalization layer, a pooling layer and the like). For example, in some cases, the output layers of the third neural network 14 may include a single convolution layer, two fully connected layers and an output layer (e.g., softmax layer). Moreover, in other cases, the output layers of the third neural network 14 may also include two convolution layers, two pooling layers, three fully connected layers, and an output layer like softmax layer (see FIG. 11).

Furthermore, in this embodiment, the third neural network 14 may include a fully connected layer, and patient information is used as inputs to the fully connected layer. In particular, for example, when the third neural network 14 has a neural network structure of a convolution layer, a pooling layer and a fully connected layer, patient information may be used as inputs to the fully connected layer (see FIG. 11). In this embodiment, when the third neural network 14 has a plurality of fully connected layers, patient information may be used as inputs to a first fully connected layer and may also be used as inputs to any other fully connected layer. In this case, the artificial neural network 10B performs diagnosis in combination with both fundus image information (feature combination information) and patient information, which is closer to the actual clinical diagnostic process of a doctor, and therefore, the accuracy of recognition of lesions in a fundus image can be improved.

It should be noted that while different method examples as mentioned before are described as a combination of a series of operations for the sake of simple description, those skilled in the art will understand that the present invention is not limited to the described sequence of operations because some steps may be performed in other sequences or simultaneously according to the present application.

In the above embodiments or examples, the description of each embodiment or example has a focus, and the parts that are not described in detail in a certain embodiment or example may refer to related descriptions of other embodiments or examples.

In addition, the method steps according to the present invention may be sequentially adjusted, merged, and deleted according to actual needs. Units or subunits in the apparatus according to the present invention may be merged, divided, and deleted according to actual needs.

One of ordinary skill in the art can understand that all or part of the steps in the above embodiments can be completed by a program to instruct related hardware, and the program can be stored in a computer readable storage medium. The storage medium includes Read-Only Memory (ROM), Random Access Memory (RAM), Programmable Read-only Memory (PROM), and Erasable Programmable Read Only Memory (EPROM), One-time Programmable Read-Only Memory (OTPROM), Electrically-Erasable Programmable Read-Only Memory (EEPROM), Compact Disc Read-Only Memory (CD-ROM) or other optical disc storage, disk storage, magnetic tape storage, or any other medium readable by a computer that can be used to carry or store data.

While the present invention is described above in detail in combination with the drawings and embodiments, it will be understood that the above descriptions do not limit the invention in any form. The present invention may be modified and changed as needed by those skilled in the art without departing from the spirit and scope of the invention, and such modifications and variations are within the scope of the invention.

Many different arrangements of the various components depicted, as well as components not shown, are possible without departing from the spirit and scope of the disclosure. Embodiments of the disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The disclosure claimed is:

1. A system for recognizing a diabetic retinopathy, comprising:
   a first neural network configured to generate a first advanced feature set from a target retinal fundus image;
   a second neural network configured to generate a second advanced feature set from a reference retinal fundus image;
   a feature combination module configured to combine the first advanced feature set and the second advanced feature set to form a feature combination set; and
   a third neural network configured to generate a diagnosis result according to the feature combination set;
   wherein:
      the target retinal fundus image and the reference retinal fundus image are taken from one person; and
      fundus images of a same resolution are used during a training process of the system.

2. The system according to claim 1, further comprising a pre-processing module configured to separately pre-process the target retinal fundus image and the reference retinal fundus image.

3. The system according to claim 1, wherein:
   the target retinal fundus image is an image of one eye of the one person; and
   the reference retinal fundus image is an image of the other eye of the one person.

4. The system according to claim 1, wherein the target retinal fundus images and the reference retinal fundus images are color images or grayscale images.

5. The system according to claim 1, wherein the first neural network and the second neural network are the same.

6. The system according to claim 1, wherein the first neural network and the second neural network are both convolutional neural network.

7. The system according to claim 1, wherein:
   the first neural network comprises a first convolutional layer, a second convolutional layer, a third convolutional layer, and a fourth convolutional layer;
   the first convolution layer uses a 5×5 convolutional kernel;
   the second convolutional layer uses a 3×3 convolutional kernel;
   the third convolutional layer uses a 3×3 convolutional kernel; and
   the fourth convolutional layer uses a 3×3 convolutional kernel.

8. The system according to claim 2, wherein the pre-processing module comprises:
   an area detection unit configured to detect designated fundus areas in the target retinal fundus image and the reference retinal fundus image;
   an adjustment unit configured to clip and resize the target retinal fundus image and the reference retinal fundus image; and
   a normalization unit configured to normalize the target retinal fundus image and the reference retinal fundus image.

9. The system according to claim 8, wherein the area detection unit detects a specific area in the retinal fundus image by at least one method selected from the group consisting of a sampling threshold method and a Hough transform method.

10. The system according to claim 8, wherein the adjustment unit is configured to resize the target fundus image and the reference fundus image to at least one size selected from the group consisting of 128×128, 256×256, 512×512, 768×768, 1024×1024, and 2048×2048 pixels.

11. The system according to claim 8, wherein the adjustment unit is configured to distinguish a retinal fundus area from a patient information area.

12. The system according to claim 8, wherein the normalization unit is configured to normalize the target retinal fundus image and the reference retinal fundus image by at least one method selected from the group consisting of a zero mean method and a unit standard deviation method.

13. The system according to claim 8, wherein the pre-processing module comprises an expansion unit configured to perform sample expansion through various transformations of the target retinal fundus image and reference fundus image.

14. The system according to claim 8, wherein:
   the pre-processing module comprises a first pre-processing module and a second pre-processing module;
   the first pre-processing module is configured to perform retinal fundus area detection, image clipping, image resizing, and image normalizing for the target retinal fundus image; and
   the second pre-processing module is configured to perform retinal fundus area detection, image clipping, image resizing, image normalizing for the reference retinal fundus image.

15. The system according to claim 1, wherein the third neural network is configured to generate the diagnosis result according to the feature combination set and the patient information.

16. The system according to claim 15, wherein the patient information comprises at least one of age, gender, eyesight, and medical history.

17. The system according to claim 1, wherein the feature combination module is configured to perform a linear transformation or a nonlinear transformation on the first advanced feature set and the second advanced feature set to obtain the feature combination set.

18. The system according to claim 1, wherein:

the first neural network is configured to generate the first advanced feature set from the target retinal fundus image using a first deep learning method; and the second neural network is configured to generate the second advanced feature set from the reference retinal fundus image using a second deep learning method; and the second deep learning method is the same as or different from the first deep learning method.

19. The system according to claim 18, wherein:

the deep learning method utilizes four fundus images including two fundus images taken from a left eye of the one person and two fundus images taken from a right eye of the one person;

the four fundus images cover specific areas of the left eye and the right eye; and the four fundus images are fundus images with a visual angle of 45 degrees.

20. The system according to claim 1, wherein:

the third neural network module is configured to output probabilities of various lesion categories;

a probability sum of the third neural network module is 1; and the third neural network module is configured to determine that a fundus has a lesion of a category when a probability of the category is the highest among various probabilities.

* * * * *